United States Patent [19]

Molloy

[11] Patent Number: 5,086,771
[45] Date of Patent: Feb. 11, 1992

[54] CONFIGURED PAD FOR THERAPEUTIC COOLING EFFECT

[75] Inventor: Michael C. Molloy, Cincinnati, Ohio

[73] Assignee: Cincinnati Sub-Zero Products, Inc., Cincinnati, Ohio

[21] Appl. No.: 755,550

[22] Filed: Sep. 5, 1991

[51] Int. Cl.$^5$ .............................................. A61F 7/00
[52] U.S. Cl. .................................. 128/400; 128/402; 128/892; 165/46
[58] Field of Search ............................... 128/399-403, 128/82.1, 40, 24.1, 379, 380, 80 C, 118.1, 882, 881, 80 C, 892; 62/530, 259.3; 165/46

[56] References Cited

U.S. PATENT DOCUMENTS

| | | | |
|---|---|---|---|
| 1,308,427 | 7/1919 | Caborde | 128/402 |
| 3,419,702 | 12/1968 | Piel | 128/402 |
| 4,108,146 | 8/1978 | Goldon | 128/402 |
| 4,149,529 | 4/1979 | Copeland et al. | 128/400 |
| 4,335,726 | 6/1982 | Kolstedt | 128/400 |
| 4,691,762 | 9/1987 | Elkins | 165/46 |
| 4,856,294 | 8/1989 | Scarhge et al. | 165/46 |
| 4,951,665 | 8/1990 | Schneider | 128/400 |
| 4,964,402 | 10/1990 | Grim et al. | 128/402 |
| 4,971,056 | 11/1990 | Seacord | 128/400 |
| 5,014,095 | 5/1991 | Benak et al. | 128/401 |

OTHER PUBLICATIONS

"3K Cryotherapy Compression Bandage" Podiatric Products, Jul. 1990, p. 14 (advertisement).

Primary Examiner—Edward M. Coven
Assistant Examiner—Mark S. Graham
Attorney, Agent, or Firm—Charles R. Wilson

[57] ABSTRACT

A configured pad for use on a body part of a patient to provide cooling is dimensioned to conform to multishapes for enhanced versatility in use. The configured pad is a substantially flattened member having a main section with generally oblong-shaped branches extending forwardly on each side and a generally circular-shaped branch extending forwardly from the main section. A cooling zone portion of the pad has an internal flow channel which extends from a lower center half area of the main section along divided halves of the first generally oblong-shaped branch, generally circular-shaped center branch and the second generally oblong-shaped branch to a second lower center half area of the main section. The configured pad has an inlet port tube and an outlet port tube positioned in the lower center area of the cooling zone portion of substantially flattened member for the flow of cooling water through the internal flow channel.

14 Claims, 3 Drawing Sheets

CONFIGURED PAD FOR THERAPEUTIC COOLING EFFECT

This invention relates to a configured pad used for therapeutic purposes. More particularly, the invention relates to a configured pad capable of conforming to multi-shapes for use on different body parts to provide cooling thereto.

Localized cold therapy is a well recognized medical procedure to heal damaged tissue. Placement of an ice pack on a damaged body part such as a twisted ankle or contusion is done routinely by medical specialists as well as by the lay person. Cold therapy is also done routinely by medical personnel to help accelerate the healing process of damaged tissue caused by surgical incisions. In fact, wound inflammation caused by any source is effectively alleviated by the use of localized cold therapy.

Ice is readily available to the lay person and is commonly used to treat minor injuries. However, ice is messy to use, ice is typically available in only one temperature which may or may not be ideal, ice readily melts and must be continually replaced and ice is difficult to position on the patient unless an ice bag or pack is available. It is not surprising that medical personnel have demanded a more controlled cold source for its needs. Apparatuses are available which provide chilled water which can be directed onto or near the patient's damaged body part. The apparatuses comprise an electrically run cold water source unit, flexible water hoses and a pad capable of receiving the chilled water. The pad is placed on the affected body part and the chilled water circulated through the pad. The water temperature is controlled and there is no mess involved in the procedure. The apparatuses available are reasonably effective.

It has been discovered that known pads used with the cold therapy apparatuses are not as effective as they should be. Most pads are configured in one shape to reasonably conform to such different body shapes as that of an ankle, knee, shoulder, torso or forehead. In effect the pad shape available is forced to fit the affected body part being treated. The result being a pad which often is difficult to position and to retain in place. The efficiency of heat transfer into the pad can also be affected if any bunching or flow-blocking folds result from trying to force-fit the pad to a particular body part configuration.

The efficiency of many pads is also adversely affected by poor water flow through the pads. Many manufacturers apparently have assumed that the pads are small enough in size that any flow through of water will be distributed substantially equally to all parts of the pad. However, for maximum efficiency and precise temperature control as demanded in certain medical situations, it is necessary that all parts of the pad which contact the body part be capable of providing the same cooling effect. A faster cooling water flow is somewhat effective, though is not ideal and does have obvious drawbacks.

Despite advances in the use of cold therapy in recent years, there is still a need by medical personnel for an effective and controlled source of cooling to damaged tissue. In particular, a pad which is capable of effectively utilizing cold water from a cooling unit is needed. In accord with this need, there has been developed a cold therapy pad which is capable of use on various body part shapes to readily fit thereon and effectively present a substantially uniform source of cooling.

SUMMARY OF THE INVENTION

A configured pad is dimensioned for ready placement on different body parts to provide a cooling therapeutic effect. The configured pad is a substantially flattened member having a main section with a first generally oblong-shaped branch extending forwardly from one side, a generally circular-shaped branch extending forwardly from a center area and a second generally oblong-shaped branch extending forwardly from another side of the main section. Formed within a cooling zone of the substantially flattened member is an internal flow channel which extends from a first lower center half area of the main section to divided halves of the first generally oblong-shaped branch, the generally circular-shaped branch, the second generally oblong-shaped branch and ultimately to a second lower center half area of the main section. A set of inlet and outlet port tubes is positioned in the lower center half areas of the main body. The port tubes are used for the flow of cooling water through the internal flow channel. The configured pad is capable of ready placement on different shaped body parts because of the shape flexibility inherent with the pad.

DETAILED DESCRIPTION OF THE INVENTION

The configured pad of the invention is described with particular reference to the drawings. The pad and its manner of use are described in the following paragraphs.

Figure 1:
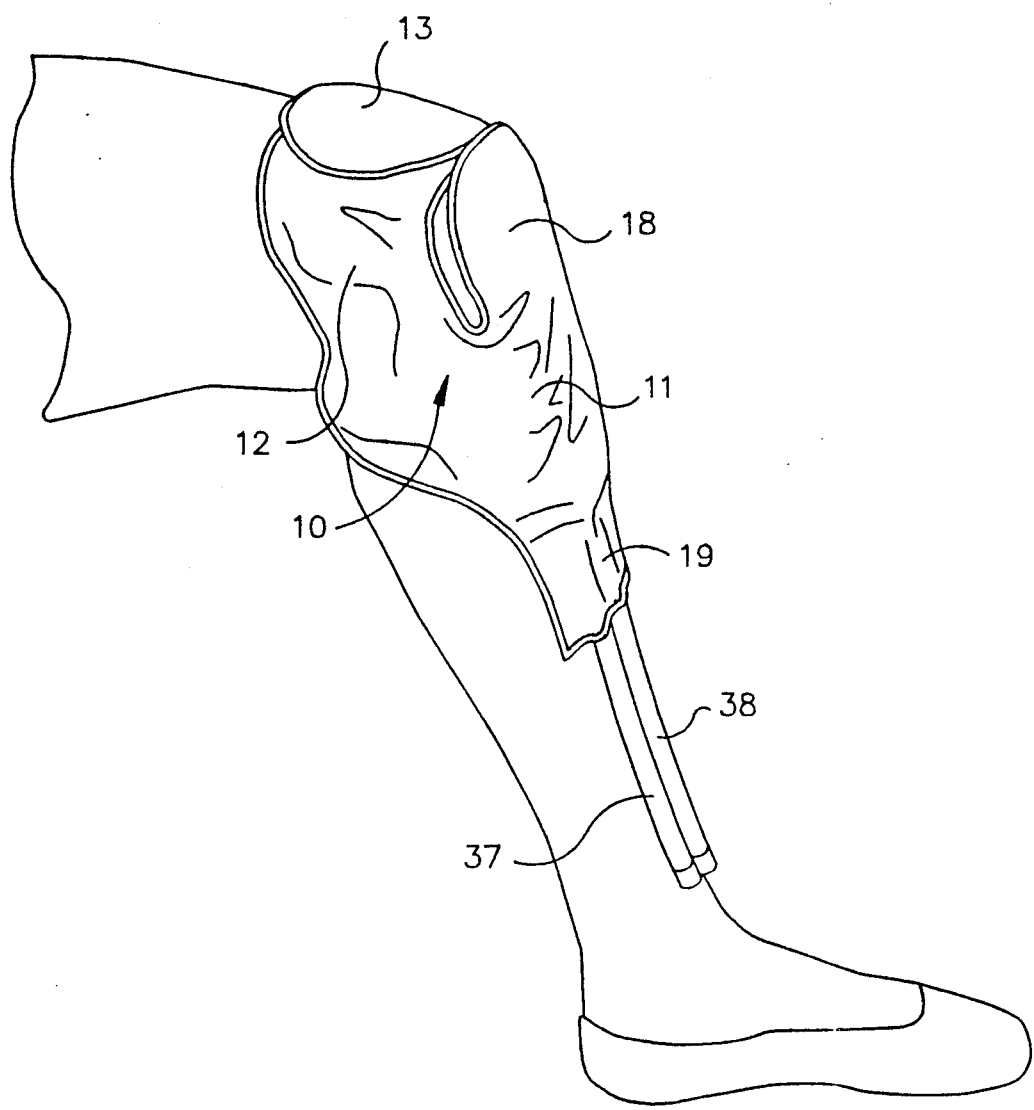
FIG. 1 in a perspective view of the configured pad of the invention positioned on the knee area of a patient.
Figure 2:
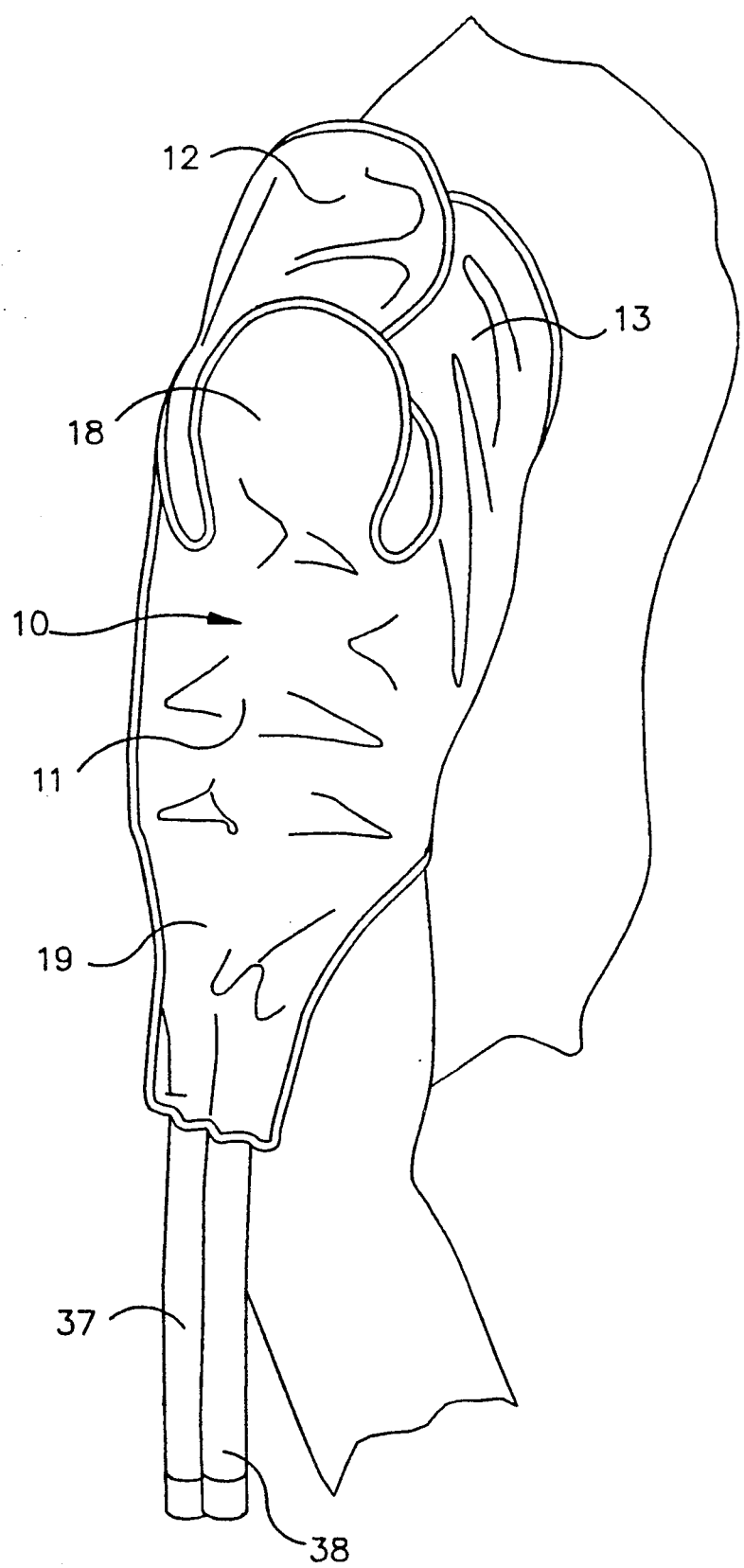
FIG. 2 is a perspective view of the configured pad shown in FIG. 1 positioned on a shoulder area of a patient.

With reference to FIGS. 1 and 2, there is shown a configured pad 10 positioned on a knee area and a shoulder area, respectively, of a patient. As evident, the pad 10 is capable of wrapping around the affected body part. It is very versatile in its use given the different shapes of a knee and shoulder. While not shown, the configured pad 10 is also adapted for use on other small movable parts of a human limb such as an ankle, elbow or hip and on more immobile body parts such as the back or head.

The configured pad 10 is a substantially flattened member with a distinct shape intended to make the pad readily usable with the various body parts of the patient. The thickness, shape and flexibility of the pad allow it to readily conform to the particular body part in a manner which provides substantially total surface contact.

Figure 3:
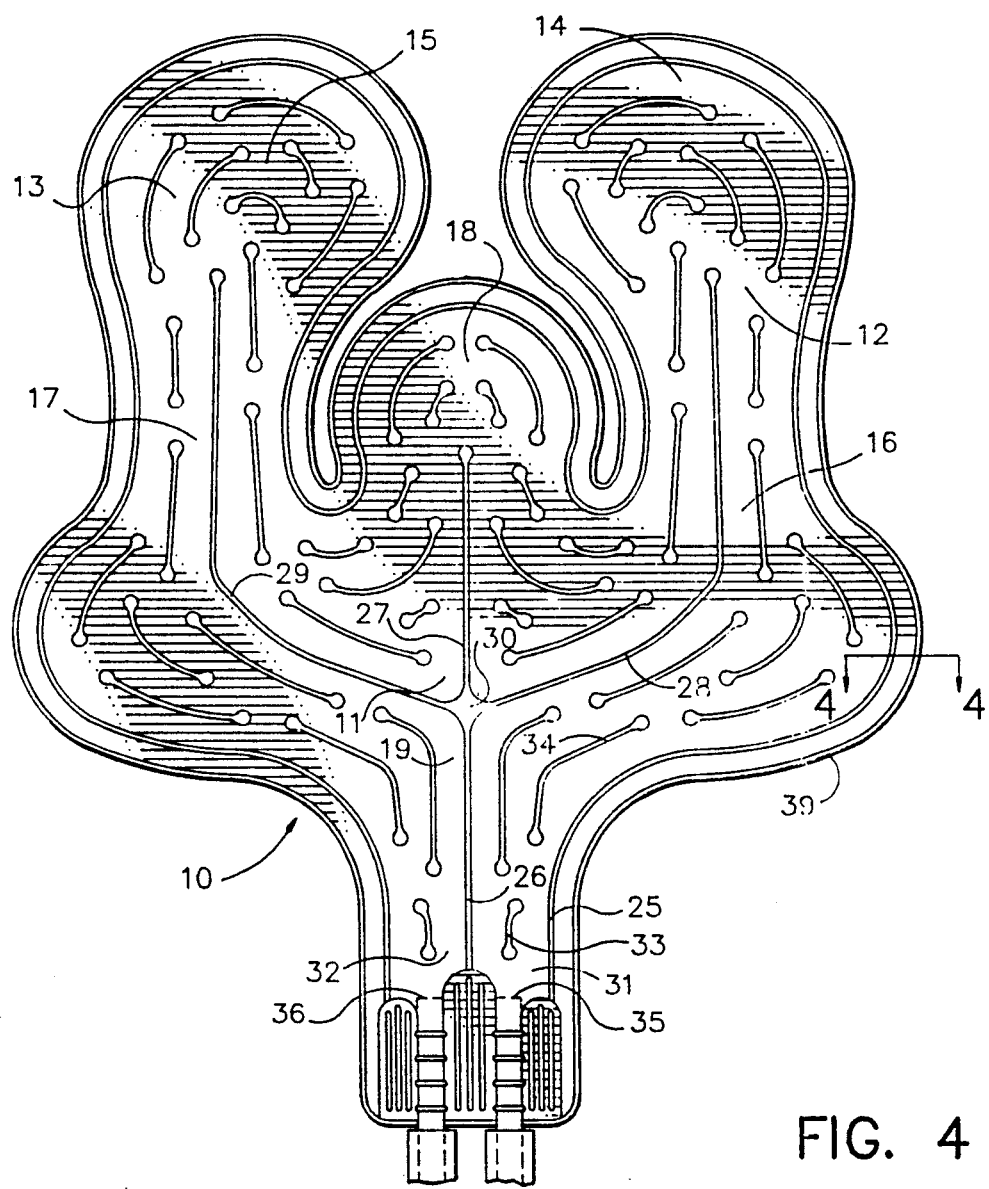
FIG. 3 is a bottom plan view of the configured pad of FIG. 1

As shown in FIGS. 1 and 2 and with particular reference to FIG. 3, the pad 10 is configured to have a main section 11 with shaped branches. A first generally oblong-shaped branch 12 extends forwardly from one side area of the main section and a second generally oblong-shaped branch 13 extends forwardly from the other side area of the main section. The generally oblong-shaped branches are curvilinear along three sides. Rounded end portions 14 and 15 of each branch are greater in width than attaching portions 16 and 17, respectively. Also extending forwardly from the main section 11 of the pad is a generally circular-shaped branch 18. This branch is rounded on three sides and extends forwardly to about the mid-length of the generally oblong-shaped branches.

A lower center area 19 of the main section 11 has inlet and outlet ports as further described below. Preferably, and as shown, the lower center area 19 is a generally rectangular-shaped branch extending downwardly from the main section of the pad.

Figure 4:
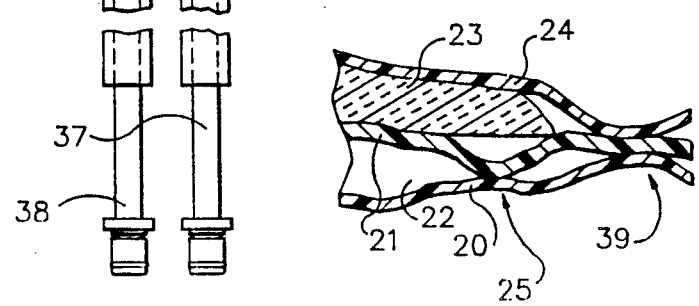
FIG. 4 is a cross-section view of the configured pad of FIG. 3 taken along line 4—4 thereof.

As best seen in FIG. 4, the cooling pad 10 is assembled so that the substantially flattened member is divided into a lower cooling zone portion and an overlying insulating zone portion. The cooling zone portion represents the side of the pad which is adjacent the patient's body part during use. The cooling zone portion comprises an outside film 20 and an inside film 21 with a periphery seal and a series of interior seals forming an internal flow channel 22. The outside face of the cooling zone portion is shown in FIG. 3. As described in detail in the following paragraphs, cooling water flows through the internal flow channel 22 to effectively cool the pad's lower surface. The insulating zone portion of the pad 10 is comprised of an insulation sheet 23 and a second outside film 24. The purpose of the insulating zone portion is to prevent or at least alleviate the formation of condensation on the upper surface of the pad during use.

The outside film 20, the inside film 21 and the second outside film 24 are all made of a water impervious synthetic polymeric material. A polyurethane film is preferred, though other polymeric films can as well be used. The thickness of the films is not critical, though a film thickness of about 4 mils to about 15 mils is preferred.

The insulation sheet 23 is a closed cell synthetic polymeric foam. Other insulation layers such as open cell polymeric foams and fibrous composites are as well usable. An insulation sheet thickness of from about 100 mils to about 250 mils is preferred for optimum insulation and pad flexibility. As shown, the insulation sheet and the second outside film are two distinct layers of materials. The two layers can also be an integral sheet of material having an inside layer of insulation material with a skin layer of wear-resistant material formed directly thereon.

The cooling zone portion of the configured pad 10 contains the internal flow channel 22 as defined by the inner peripheral seal 25 which extends completely around the pad and the series of interior seals. The internal flow channel 22 extends throughout the cooling zone portion and essentially covers the entire bottom side of the pad. FIG. 3 depicts the outlines of the internal flow channel. The flow channel is defined by the inner peripheral seal 25 extending completely around the cooling zone portion of the flattened member and interior seals 26, 27, 28 and 29. A lower center seal 26 extends from the periphery seal in the lower center area of the main section to an approximate center point 30 of the main section. An upper center seal 27 extends from the approximate center point 30 to a mid-portion of the generally circular-shaped branch 18. The center seals 26 and 27 divide the cooling zone into substantially equal halves.

A side seal 28 extends from the approximate center point 30 of the main section to near the rounded end portion 14 of the first generally oblong-shaped branch 12. The seal 28 is curved to generally follow the periphery of the pad to divide one side of the main section and the first oblong-shaped branch 12 into substantially equal halves. Another interior side seal 29 also extends from the approximate center point 30 to near the rounded end portion 15 of the second generally oblong-shaped branch 13. The point 30 where the two side seals 28 and 29 meet the lower and upper center seals 26 and 27 is the approximate center point of the configured pad. Four sections of irregular shape, though substantially equal volume are formed by the interior seals.

The internal flow channel of the substantially flattened member's cooling zone is defined by the seals. The channel starts at a lower center half area 31 of the lower center area 19 of the main section 11 and is initially defined by the center seal 26 and the inner periphery seal 25 until it reaches the approximate area of the center point 30. The channel is then defined by the side seal 28 and periphery seal 25 and extends along the generally oblong-shaped branch 12 to near the rounded end portion 14. The channel follows down the other half of the branch as defined still by the side seal 28 and periphery seal 25 until the approximate area of the center point 30 is reached. The channel continues into the generally circular-shaped branch 18 as defined by the upper center seal 27 and periphery seal 25 to complete its journey through an approximate half of the cooling zone portion of the flattened member. The channel leads into the other approximate half of the cooling zone portion as defined always by the periphery seal 25 and sequentially by the upper center seal 27, side seal 29 along both sides thereof, and finally the lower center seal 26 until the second lower center half area 32 of the lower center area 19 is reached.

A series of expansion limiting island seals 33 are interspersed throughout the internal flow channel. The island seals prevent the substantially flattened body from excessively expanding due to the water pressure of the cooling water. The substantially flattened state of the configured pad is desired for maximum heat transference and optimum shaping around the particular body part of the patient. The island seals also direct the flow of water through the channel to ensure against pockets of stagnant or relatively slow moving water in the channel.

The expansion limiting island seals 33 are elongated seals which extend along the length of the flow channel. Preferably, one elongated seal is provided per lateral inch of channel. Preferably, certain of the island seals are also curvilinear and positioned in the internal flow channel where a change of flow direction occurs. Thus, the curvilinear island seal 34 is curved such that the seal itself follows the contour of the channel at its point of placement. The curvilinear nature of these seals direct the smooth flow of water around the channel as it changes course.

Located at the lower center half areas 31 and 32 of the pad are an inlet port 35 and an outlet port 36. The ports are opened to the internal flow channel. An inlet tube 37 and an outlet tube 38 are tubular-shaped members which are sealed into the ports of the respective inlet and outlet ports of the pad so as to be in communication with the internal flow channel. Each end of the two tubes has means to receive a cooling water hose and a drain hose in a liquid tight manner. Mechanical connecting means such as a slip fitting, threaded connector or band clamp are used to provide the liquid tight seal.

The configured pad of the invention is readily assembled by the manufacturer. The films used to form the cooling zone portion of the pad are die cut to the proper shape. Inlet and outlet tubes are properly positioned between the films. The components are then subjected to a sealing process to form the interior periphery seal and the interior seals, including the island seals and to seal the tubes in place. Any means of sealing can be used, including heat sealing and radio frequency sealing. Next, the insulation sheet and the outside film forming the insulating zone are positioned over the formed cooling zone portion. The assembled layers are the subject of a second sealing process to form an outer periphery seal 39 at the edge of the three films. The insulation sheet is effectively trapped between the films.

In operation, the configured pad is positioned on the body part of the patient needing cold therapy such that the cooling zone portion is adjacent the body part. The main section of the pad is basically placed to cover a center portion of the body part. Care is taken to ensure that the inlet and outlet ports found in the lower center area of the main body are accessible. Next, the generally oblong-shaped and circular-shaped branches are wrapped around the sides of body parts such that the main section and the three branches form a continuous surface over the body part. Next, a water hose leading from a cooling unit is connected to the inlet port. A return or drain hose is connected to the outlet port. The cooling unit is turned on. Cooled water flows through the inlet port, through the internal flow channel and eventually exits through the outlet port. The cold therapy is continued as long as deemed necessary by the medical personnel.

While the invention has been described with particular reference to the drawings, it should be understood obvious modifications and variations can be made to the configured pad. All such changes are considered within the scope of the appended claims.

I claim:

1. A configured pad for placement on a body part of a patient so as to conform thereto for the purpose of effectively cooling the body part, said configured pad comprising:

(a) a substantially flattened member having a main section, a first generally oblong-shaped branch extending forwardly from a side area thereof, a generally circular-shaped branch extending forwardly from an upper center area thereof and a second generally oblong-shaped branch extending forwardly from another side area thereof, wherein said substantially flattened member is divided into a lower cooling zone portion and an overlying insulating zone portion, said lower cooling zone portion having formed therewithin an internal flow channel extending generally from a lower center area of the main section along divided halves of the first generally oblong-shaped branch, the generally circular-shaped branch and the second generally oblong-shaped branch back to the lower center area of the main section; and (b) inlet and outlet port tubes located in the lower center area of the main section in communication with the internal flow channel such that cooling water which enters the inlet port tube flows through the internal flow channel to provide a cooling effect to the body part adjacent the configured pad and ultimately flows out the outlet port tube.

2. The configured pad of claim 1 wherein the cooling zone portion of the substantially flattened member is formed of a lower film of water impervious material and an upper film of water impervious material sealed together along peripheries thereof and further selectively sealed along interior portions thereof to form the internal flow channel.

3. The configured pad of claim 2 wherein each of the water impervious films is a synthetic polymeric film.

4. The configured pad of claim 3 wherein each of the synthetic polymeric films is a polyurethane film.

5. The configured pad of claim 4 wherein the insulating zone portion is formed of an insulation sheet and a water impervious film.

6. The configured pad of claim 5 wherein the insulation sheet is a synthetic polymeric foam.

7. The configured pad of claim 1 wherein the main section of the flattened member has a generally rectangular-shaped branch which extends downwardly therefrom to form the lower center area.

8. The configured pad of claim 7 wherein the generally circular-shaped branch extends forwardly to about mid-length of the generally oblong-shaped branches.

9. The configured pad of claim 8 wherein the cooling zone portion has a center seal which extends from a sealed periphery of the lower center area of the main section to an approximate center point of the main section to divide said cooling zone portion into two substantially equal halves and further wherein side seals extend from the approximate center point outwardly to near an end portion of each of the first and second generally oblong-shaped branches to divide each said branch into substantially equal halves.

10. The configured pad of claim 1 wherein the internal flow channel has a series of expansion limiting island seals interspersed throughout to prevent an excessive expansion of the substantially flattened member during use.

11. The configured pad of claim 10 wherein the expansion limiting island seals are elongated seals which extend along the length of the internal flow channel.

12. The configured pad of claim 11 wherein at least one elongated seal per lateral inch of the internal flow channel is provided.

13. The configured pad of claim 1 wherein the inlet port tube and the outlet port tube are sealed into the cooling zone portion of the substantially flattened member.

14. The configured pad of claim 1 wherein the substantially flattened member is sufficiently flexible to allow the generally oblong-shaped branches and circular-shaped branch to fold around a part of a human limb to cover at least three sides thereof.

* * * * *